(12) United States Patent
Jacovella

(10) Patent No.: US 10,376,492 B2
(45) Date of Patent: Aug. 13, 2019

(54) USE OF A MACROCYCLIC LACTONE FOR TREATING A COMPLICATION FROM A PAPILLOMA VIRUS INFECTION

(71) Applicant: GALDERMA S.A., Cham (CH)

(72) Inventor: Jean Jacovella, Antibes (FR)

(73) Assignee: GALDERMA S.A., Cham (CH)

( * ) Notice: Subject to any disclaimer, the term of this patent is extended or adjusted under 35 U.S.C. 154(b) by 0 days.

(21) Appl. No.: 14/780,314

(22) PCT Filed: Mar. 28, 2014

(86) PCT No.: PCT/EP2014/056374
§ 371 (c)(1),
(2) Date: Sep. 25, 2015

(87) PCT Pub. No.: WO2014/154899
PCT Pub. Date: Oct. 2, 2014

(65) Prior Publication Data
US 2016/0051508 A1 Feb. 25, 2016

(30) Foreign Application Priority Data
Mar. 29, 2013 (FR) ...................... 13 52855

(51) Int. Cl.
*A61K 31/365* (2006.01)
*A61K 31/7048* (2006.01)

(52) U.S. Cl.
CPC ........ *A61K 31/365* (2013.01); *A61K 31/7048* (2013.01)

(58) Field of Classification Search
CPC .................... A61K 31/365; A61K 31/7048
See application file for complete search history.

(56) References Cited

U.S. PATENT DOCUMENTS 7,550,440 B2 * 6/2009 Manetta ............... A61K 9/0014
514/30

FOREIGN PATENT DOCUMENTS

| WO | 2010/072958 A2 | 7/2010 |
| WO | 2012/054334 A1 | 4/2012 |
| WO | 2012/150543 A1 | 11/2012 |

OTHER PUBLICATIONS

Namekawa et al., Proc. Japan Acad., 1998, 74 Ser. B, p. 65-68.*
Sigma-Aldrich MSDS for 16-hexadecanolide, Sigma-Aldrich Corporation, Revision Date Jun. 27, 2014, Print Date Apr. 13, 2017.*
Uren et al., Cancer Res., 2005, 65(14), p. 6199-6206.*
Spartz et al., Virology, 2005, 336, p. 11-25.*
Drinyaev et al., Eur. J. Phramacol., 2004, 501, p. 19-23. (Year: 2004).*
Ramachandran et al., Oncogene, 2012, 31, p. 2725-2737, published online Oct. 17, 2011. (Year: 2011).*
NCI Dictionary of Cancer Terms, dysplasia, https://www.cancer.gov/publications/dictionaries/cancer-terms/def/dysplasia, accessed online on Nov. 7, 2018. (Year: 2018).*
International Search Report and Written Opinion dated Jun. 4, 2014 corresponding to International Patent Application No. PCT/EP2014/056374, 11 pages.
English Translation of the International Search Report dated Jun. 4, 2014 corresponding to International Patent Application No. PCT/EP2014/056374, 3 pages.
Menzo et al., "Human papillomavirus infections: new perspectives for prevention and treatment introduction", New Microbiologica, Jan. 1, 2007, pp. 189-212.
Borku et al., "Ivermectin is an effective treatment for bovine cutaneous papilomatosis", Research in Veterinary Science, Brithsh Veterinary Association, vol. 83, No. 3, Sep. 14, 2007, pp. 360-363.
Aslan et al., "Is it Possible to Treat Equine Papillomatosis with Ivermectin Given Orally?", vol. 16, No. 6, 2010, pp. 1065-1068.

* cited by examiner

*Primary Examiner* — Jonathan S Lau
(74) *Attorney, Agent, or Firm* — Sunit Talapatra; Foley & Lardner LLP

(57) ABSTRACT

A compound is described that is selected from among macrocyclic lactones for treating and/or preventing a complication from a human papillomavirus infection. The complication to be treated and/or prevented can be selected from among malignant melanomas, skin carcinomas, in situ or invasive carcinomas, epidermoid carcinomas, Bowen's disease, head and neck cancers, upper aerodigestive tract cancers, laryngeal cancers, esophageal cancers, stomach cancers, oral papillomas, pharyngeal papillomas, laryngeal papillomas, esophageal papillomas, lung cancers, intravulval neoplasias, intravaginal neoplasias, intracervical neoplasias, cervical dysplasias, cervical carcinomas, penile cancer, intrapenile neoplasias, and in situ or invasive anal carcinomas.

18 Claims, No Drawings

USE OF A MACROCYCLIC LACTONE FOR TREATING A COMPLICATION FROM A PAPILLOMA VIRUS INFECTION

CROSS-REFERENCE TO PRIOR APPLICATIONS

This application is a National Stage of PCT/EP2014/056374, filed Mar. 28, 2014, and designating the United States (published on Oct. 2, 2014, as WO 2014/154899 A1), which claims priority under 35 U.S.C. § 119 to French Patent Application No. 1352855, filed Mar. 29, 2013, each hereby expressly incorporated by reference in its entirety and each assigned to the assignee hereof.

The object of the present invention is a compound selected from macrocyclic lactones for its use for treating and/or preventing a complication of an infection by a human papilloma virus.

Papilloma viruses belong to the family of Papovaviridae (genus *Papillomaviridae*). These are viruses of a small size (from 50 to 55 nm in diameter), consisting of a nucleocapsid of 72 capsomers. Their genome consists of a double-strand DNA molecule with about 8,000 base pairs. These viruses have been identified, in many species of mammals, in birds and reptiles. However, the papilloma viruses are highly specific of the host species, and no infection crossed with other species has been observed ("Infections with papilloma viruses", Encyclopédie Médico-Chirurgicale, 2004, 8-054-A-10).

Papilloma viruses have particular tissue tropism for skin and squamous mucosas. The papilloma viruses infecting humans ("human papilloma virus" or HPV) are thus associated with specific anatomic localizations and with characteristic lesions. However, these localizations are not exclusive since under certain conditions, like in the case of immunodepression, usually genital papilloma viruses may be found associated with skin lesions for example. The infections of the skin or of the mucosas and their complications may thus affect the hands, the feet, the limbs, the trunk, the head, the neck, the face or further anogenital, oral and laryngeal mucosas.

The HPVs play an etiological role in the development of precancer and cancer lesions. Suggested since 1976, this link was confirmed in the middle of the 90s, by means of molecular biology techniques, notably between certain HPVs (notably HPV 16 and 18) and cancers of the uterine cervix.

Today, no treatment exists allowing destruction of the viruses.

Visible lesions may however be suppressed in a more or less simple way. Lesions of the uterine cervix, for example, are treated by cryotherapy, by laser, or even by surgery (ablation of a portion or of the totality of the uterine cervix). In order to suppress condylomas (or genital warts), local medicinal treatments exist, notably based on podophyllotoxin, of trichloroacetic acid or imiquimod. In order to be efficient, these actives require extended application over time. Other treatments exist such as physical treatments such as laser vaporization, curetted electrocoagulation or cryotherapy. These treatments may have the drawback of leaving scars after treatment. Further, present treatments are essentially based on the destruction of the infected cells and not of the virus itself. Insofar that the infra-clinical infection is not detectable (i.e., without any visible clinical signs), these treatments are carried out only on the actual lesions and not on a sufficiently wide surface area for avoiding relapses.

Further, the treatments of the HPVs described earlier have drawbacks such as irritation and intolerance phenomena, notably when they are used in a prolonged way. On the other hand, these treatments are only suppressive and not curative, notably by acting on the visible lesions and not on the infection per se.

The ideal treatment of HPVs requires prolonged use and this in a safe and efficient way.

Taking into account the foregoing, therefore, there exists a need for finding an active which exhibits improved efficiency in the treatment of the complications of infections due to the HPVs, and which does not have the secondary effects described in the prior art.

The object of the present invention is thus a compound selected from macrocyclic lactones for its use for treating and/or preventing a complication of an infection by a human papilloma virus selected from malignant melanomas, skin carcinomas, in-situ or invasive carcinomas, epidermoid carcinomas, Bowen's disease, head and neck cancers, cancers of the upper aerodigestive tracts, larynx cancers, oesophagus cancers, stomach cancers, buccal papillomas, pharyngeal papillomas, laryngeal papillomas, oesophageal papillomas, lung cancers, vulvar intraepithelial neoplasias, vaginal intraepithelial neoplasias, cervical intraepithelial neoplasias, cervical dysplasias, carcinomas of the uterine cervix, penile cancer, penile intraepithelial neoplasias, anal in-situ or invasive carcinomas.

In a preferred embodiment, the complications of an infection by a human papilloma virus are selected from malignant melanomas, skin carcinomas, in-situ or invasive carcinomas, epidermoid carcinomas, Bowen's disease, head and neck cancers.

The invention also relates to the use of a compound selected from macrocyclic lactones or pharmaceutically acceptable salts thereof for preparing a drug for treating complications of an infection by a human papilloma virus as defined above.

The invention also relates to a method comprising the administration of a compound selected from macrocyclic lactones or their pharmaceutically acceptable salts in a patient for treating the complications of an infection by a human papilloma virus as defined above.

In an embodiment, the term of "treatment" or "treat" refers to an improvement, prophylaxis of a disease or of a disorder, or of at least one symptom which may be distinguished from the latter. In another embodiment, "treatment" or "treat" refers to an improvement, prophylaxis of at least one measurable physical parameter associated with the disease or disorder being treated, which is not necessarily distinguishable in or by the treated subject.

In another additional embodiment, "treatment" or "treat" refers to inhibition or slowing down of the progression of a disease or disorder, physically, for example, stabilization of a physiologically distinguishable symptom, for example, the stabilization of a physical parameter, or both. In another embodiment, "treatment" or "treat" refers to the delay in the occurrence of a disease or disorder.

In certain embodiments, compounds of interest are administered as a preventive measure. In the present context, "prevention" or "prevent" refers to a reduction in the risk of acquiring a disease or a specified disorder.

The patient is a human patient, a man or woman.

According to the invention, the human papilloma virus is any kind of HPV. Preferably, the human papilloma virus is selected from HPV-1, HPV-2, HPV-3, HPV-4, HPV-5, HPV-6, HPV-7, HPV-8, HPV-11, HPV-16, HPV-18, HPV-31, HPV-33 and HPV-35.

Macrocyclic lactones are preferably selected from avermectins and milbemycins.

The families of avermectins and milbemycins are a group of macrocyclic lactones produced by the bacteria *Streptomyces avermitilis* (Reynolds J E F (Ed) (1993) Martindale. The extra pharmacopoeia. 29$^{th}$ Edition. Pharmaceutical Press, London). Among the avermectins, ivermectin is found.

Natural avermectins are a series of macrocyclic lactones with 16 members isolated from fermentation products of *Streptomyces avermitilis*.

The compounds from the family of avermectins which may be used according to the present invention may be selected from ivermectin, avermectin A[1a], avermectin A[1b], avermectin A[2a], avermectin A[2b], avermectin B[1a], avermectin B[1b], avermectin B[2a], avermectin B[2b], emamectin, abamectin, doramectin, eprinomectin, latidectin and selamectin.

Preferentially, the compound of the family of avermectins is ivermectin. In the present context, ivermectin is a mixture of 22,23-dihydroavermectin $B_{1a}$ and 22,23-dihydroavermectin $B_{1b}$. Ivermectin contains in majority 22,23-dihydroavermectin $B_{1a}$.

The compounds of the family of milbemycins which may be used according to the present invention may be selected from milbemycin, lepimectin, milbemectin, milbemycin oxime, moxidectin and nemadectin.

Preferentially, the compound of the family of milbemycins is milbemycin.

The pharmaceutically acceptable salts of the compounds of the invention are also comprised in the invention.

The expression "pharmaceutically acceptable salt(s)", in the present context, refers to salts of a compound of interest, preferably for topical use, and which have the desired biological activity. Pharmaceutically acceptable salts comprise salts of acid or basic groups present in the specified compounds. Pharmaceutically acceptable acid addition salts comprise, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Suitable basic salts comprise, but are not limited to, salts of aluminium, calcium, lithium, magnesium, potassium, sodium, zinc, and diethanolamine. For a review on pharmaceutically acceptable salts, see Berge et al. (J Pharm Sci. 1977 January; 66(1):1-19).

By antiviral action, the macrocyclic lactone according to the invention gives the possibility of treating the complications of an infection by a human papilloma virus.

By its penetration on the actual location of viral multiplication of HPVs, the macrocyclic lactone according to the invention gives the possibility of preventing complications due to infections by HPV.

Indeed, when HPV penetrates into the germinal cells of the epithelial basal layer, subsequent to a microlesion, it multiplies in the tissue, by benefitting from the differentiation of keratinocytes. Thus, viral multiplication with complete synthesis of the virion is only observed in the most superficial layers of the epidermis, when the cell is well differentiated. During early stages of the infection, the viral genome is multiplied in the basal layers of the epithelium in an episomal form, in an amount of 50 to 100 copies per cell. This step does not seem to be specific to the tissue. On the other hand, the establishment of the productive viral cycle involves modification of the host cell, the viral production only being possible in differentiated keratinocytes.

The cytopathogenic effect is characterized by koilocytosis; this is a cell of the intermediate or outmost layers with an oedematous nucleus, irregular chromatin (a sign of viral activity) and especially the existence of a perinuclear intracytoplasm vacuola pushing back the cytoplasm to the periphery; this vacuola seems optically empty. At a tissue scale, epithelial proliferation and architectural modification are noted with occurrence of micropapillas. There exist large variations in the produced amount of viruses, depending on the site and on the nature of the lesions.

By a targeted action, topical administration of a macrocyclic lactone according to the invention entails treatment and/or prevention of the complications of an infection by a human papilloma virus in humans, women and children.

Typically, the complications of infections by HPV are selected from malignant melanomas, skin carcinomas, in-situ or invasive carcinomas, epidermoid carcinomas, Bowen's disease, head and neck cancers (notably eyes, cornea, eyelids, ears, lips and oral cavity—tongue, gums, the floor of the mouth and palate), cancers of upper aerodigestive tracts (notably oropharynx, nasopharynx, hypopharynx, nasal cavity, paranasal sinus, salivary glands and tonsils), cancers of the larynx, cancers of the oesophagus, cancers of the stomach, buccal papillomas, pharyngeal papillomas, laryngeal papillomas, oesophageal papillomas, lung cancers, vulvar intraepithelial neoplasias, vaginal intraepithelial neoplasias, cervical intraepithelial neoplasias, cervical dysplasias, carcinomas of the uterine cervix, penile cancer, penile intraepithelial neoplasias, and anal in-situ or invasive carcinomas.

Preferentially, the complications of infections by HPV are selected from malignant melanomas, skin carcinomas, in-situ or invasive carcinomas, epidermoid carcinomas, Bowen's disease, head and neck cancers.

In the compositions according to the invention, said compound from the family of avermectins or milbemycins is present in a composition, and represents between 0.001 and 10% by weight based on the total weight of the composition, preferably between 0.01 and 5% by weight. In the whole of the present text, unless specified otherwise, it is understood that when concentration intervals are given, they include the upper and lower limits of said interval.

The composition comprises, in addition to the compound from the family of avermectins or milbemycins, a pharmaceutically or physiologically acceptable medium.

In the case of topical or mucosal administration, this means any medium compatible with the skin, the mucosas and/or appendages.

Advantageously, the compositions of the invention comprise, in addition to at least one compound from the family of avermectins or milbemycins, at least one other therapeutic agent which may increase the efficiency of the treatment.

As non-limiting examples of such agents, mention may be made of antibiotics, antibacterial agents, antiviral agents, antiparasite agents, antifungal agents, anaesthetics, analgesics, keratolytics like trichloroacetic acid, podophyllotoxin, immunostimulating products of the imiquimod type, or a mixture thereof.

The compositions according to the invention may further comprise any adjuvant customarily used in the dermatological field, compatible with said compound from the family of avermectins or milbemycins. In particular in the preferred case of a skin application, mention may notably be made of chelating agents, antioxidants, solar filters, preservatives, fillers, electrolytes, humectants, coloring agents, usual either mineral or organic bases or acids, perfumes, moisturizers, vitamins, sphingolipids, self-tanning compounds, soothing and protective agents of the skin, pro-penetrating agents, gelling agents or a mixture thereof. These adjuvants, as well as their concentration should be such that they are not detrimental to the advantageous properties of the mixture according to the invention. These additives may be present in the composition in an amount from 0 to 20% by weight based on the total weight of the composition, preferably from 1 to 10% by weight.

As preservatives, as an example, mention may be made of benzalkonium chloride, phenoxyethanol, benzyl alcohol, diazolidinyl urea, parabens or mixtures thereof.

As humectant agents, mention may in particular be made of glycerol and sorbitol.

As chelating agents, as an example, mention may be made of ethylenediamine-tetraacetic acid (EDTA), as well as its derivatives or its salts, dihydroxyethylglycine, citric acid, tartaric acid or mixtures thereof.

As pro-penetrating agents, mention may in particular be made of propylene glycol, dipropylene glycol, propylene glycol dipelargonate, lauroglycol and ethoxydiglycol.

The compound according to present invention, and the composition comprising it, may be administered via a topical, vaginal, rectal, oropharyngeal, nasal, ocular, auricular, enteral or parenteral route.

They are preferably administered via topical application.

By topical route, pharmaceutical compositions, which are therefore more particularly intended for treating the skin, may appear as ointments, creams, milks, pomades, powders, impregnated buffers, solutions, gels, sprays, lotions or suspensions. They may also appear as microspheres or nanospheres or lipid or polymeric vesicles or polymeric patches and hydrogels allowing controlled release of the active ingredients. These compositions via a topical route may moreover appear in an anhydrous form, or in an aqueous form.

Via a vaginal route, the compositions according to the invention may be applied in the form of vaginal tablets.

Via a rectal route, the compositions according to the invention may be applied in the form of creams or suppositories.

Via an oropharyngeal, nasal, or auricular route, the compositions according to the invention may be applied as liquid compositions of the suspension or lotion type.

Via a parenteral route, the compositions according to the invention may be applied via a subcutaneous or intradermal route. As a non-limiting example of parenteral preparations, mention may be made of preparations in the form of solutions or suspensions for perfusion or for injection.

Via an enteral route, the compositions may appear as tablets, gelatin capsules, dragees, syrups, suspensions, solutions, powders, granules, emulsions, microspheres or nanospheres or lipid or polymeric vesicles allowing controlled release.

Via an ocular route, these are mainly eyedrops.

The actually administered amount to be applied according to the invention depends on the sought therapeutic or cosmetic effect, and may therefore vary to a great extent. One skilled in the art, in particular the physician may easily, on the basis of his/her general knowledge, determine the suitable amounts. Thus, and according to a preferred embodiment, the pharmaceutical composition(s) are administered once to twice a day. Preferably, the treatment may have a duration ranging from 1 week to 6 months, renewable, preferably from 2 weeks to 4 months. The cures may be renewed in cycles with or without a rest period.

In the compositions according to the invention, the daily dose of administered compounds of the invention is from 100 µg to 1 g, preferably from 150 µg to 500 mg, still preferably from 200 µg to 150 mg.

The invention claimed is:

1. A method of treating a complication of an infection by a human papilloma virus selected from the group consisting of vaginal intraepithelial neoplasias, cervical intraepithelial neoplasias, and cervical dysplasias, the method comprising administering topically a pharmaceutical composition comprising from 100 µg to 500 mg of an avermectin, milbemycin, or pharmaceutically acceptable salt thereof, to an adult human patient in need thereof.

2. The method according to claim 1, wherein the avermectin is selected from the group consisting of ivermectin, avermectin A[1a], avermectin A[1b], avermectin A[2a], avermectin A[2b], avermectin B[1a], avermectin B[1b], avermectin B[2a], avermectin B[2b], emamectin, abamectin, doramectin, eprinomectin, latidectin and selamectin.

3. The method according to one claim 1, wherein the milbemycin is selected from the group consisting of milbemycin, lepimectin, milbemectin, milbemycin oxime, moxidectin and nemadectin.

4. The method according to claim 1, wherein the avermectin is ivermectin.

5. The method according to claim 1, wherein the avermectin, milbemycin, or salt thereof, is present in the pharmaceutical composition in an amount from 150 µg to 500 mg.

6. The method according to claim 1, wherein the human papilloma virus is selected from the group consisting of HPV-1, HPV-2, HPV-3, HPV-4, HPV-5, HPV-6, HPV-7, HPV-8, HPV-11, HPV-16, HPV-18, HPV-31, HPV-33 and HPV-35.

7. The method according to claim 5, wherein the avermectin, milbemycin, or salt thereof, is present in an amount from 0.001% to 10% by weight based on the total weight of the composition.

8. The method according to claim 5, wherein the avermectin, milbemycin, or salt thereof, is present in an amount from 0.01% to 5% by weight of the composition.

9. The method according to claim 1, wherein the complication is vaginal intraepithelial neoplasias and/or cervical intraepithelial neoplasias.

10. The method according to claim 1, wherein the composition further comprises at least one other therapeutic agent selected from the group consisting of an antibiotic, an antibacterial agent, an antiviral agent, an antiparasitic agent, an antifungal agent, an anesthetic, an analgesic, a keratolytic, a podophyllotoxin, and an immunostimulating product of the imiquimod type.

11. The method according to claim 1, wherein the composition is administered once a day.

12. The method according to claim 1, wherein the treatment is from 1 week to 6 months.

13. The method according to claim 1, wherein the treatment is from 2 weeks to 4 months.

14. The method according to claim 1, wherein the composition is administered twice a day.

15. The method according to claim 1, wherein the treatment is from 1 week to 6 months.

16. The method according to claim 1, wherein the treatment is from 2 weeks to 4 months.

17. The method according to claim 1, wherein the pharmaceutical composition is administered intravaginally.

18. The method according to claim 1, wherein the pharmaceutical composition further comprises at least one additive selected from the group consisting of a chelating agent, an antioxidant, a solar filter, a preservative, a filler, an electrolyte, a humectant, a coloring agent, a perfume, a moisturizer, a vitamin, a sphingolipid, a self-tanning compound, a soothing and protective agent of the skin, a pro-penetrating agent, and a gelling agent.

* * * * *